United States Patent [19]
Phillips

[11] Patent Number: 5,611,429
[45] Date of Patent: Mar. 18, 1997

[54] MEDICAL SYRINGE DISPOSAL

[76] Inventor: Paul B. Phillips, P.O. Box 273510, Tampa, Fla. 33688-3510

[21] Appl. No.: 416,642

[22] Filed: Apr. 5, 1995

[51] Int. Cl.$^6$ ........................................ B65D 83/10
[52] U.S. Cl. .................... 206/365; 206/363; 206/306; 206/524.4
[58] Field of Search ..................... 206/306, 363, 206/364, 365, 524.3, 524.9, 524.4

[56] References Cited

U.S. PATENT DOCUMENTS

| | | | |
|---|---|---|---|
| 3,021,942 | 2/1962 | Hamilton | 206/365 |
| 3,367,488 | 2/1968 | Hamiton | 206/365 |
| 3,434,587 | 3/1969 | Ciampa | 206/365 |
| 3,608,769 | 9/1971 | Gablin . | |
| 3,934,722 | 1/1976 | Goldberg | 206/365 |
| 4,022,317 | 5/1977 | Burgeson . | |
| 4,382,512 | 5/1983 | Furminger . | |
| 4,562,001 | 12/1985 | Vietzke et al. . | |
| 4,756,407 | 7/1988 | Larsen . | |
| 4,847,505 | 7/1989 | Suthanthiran . | |
| 4,871,077 | 10/1989 | Ogden et al. . | |
| 4,872,563 | 10/1989 | Warder | 206/524.3 |
| 4,892,525 | 1/1990 | Hermann, Jr. et al. | 206/365 |
| 4,921,096 | 5/1990 | McFarlane | 206/363 |
| 5,277,312 | 1/1994 | Vumbaca | 206/370 |

FOREIGN PATENT DOCUMENTS 1008136  2/1952  France ....................... 206/365

Primary Examiner—David T. Fidei
Attorney, Agent, or Firm—Charles A. McClure

[57] ABSTRACT

Disposal of used medical syringes individually, with or without attached needles, is accomplished by placement in individual fluid leakproof containers and, if any residual radioactive content, also by placement of such container and contents within another container effective to shield the surroundings against radiation therefrom. The inner container is assembled from two tubular pieces, preferably by press-fitting them together into an audible and tactile snap-fit. The outer container is assembled from two larger tubular pieces, as by twist-fitting them together, thus enclosing the inner container, with the inner container enclosing a used syringe and any contents.

6 Claims, 2 Drawing Sheets

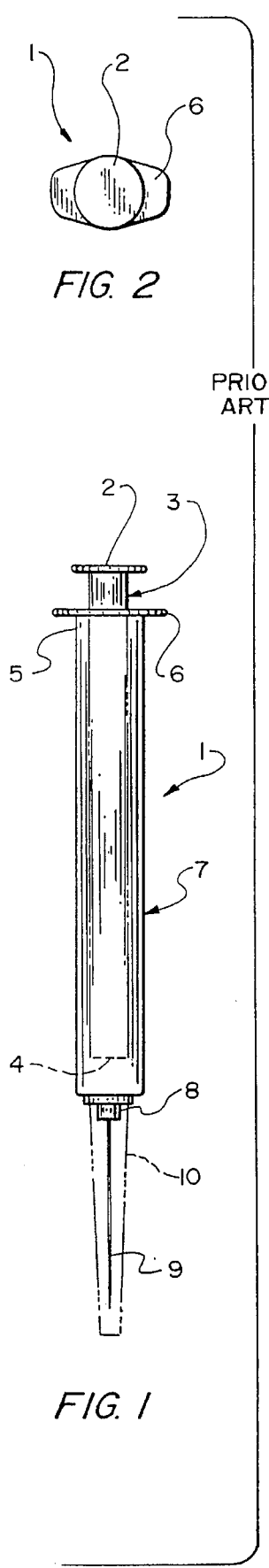
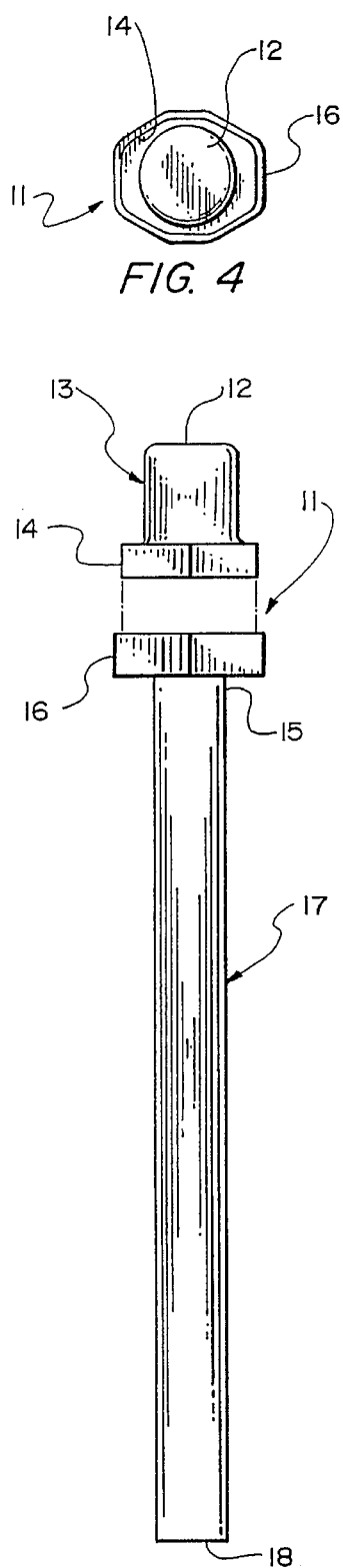
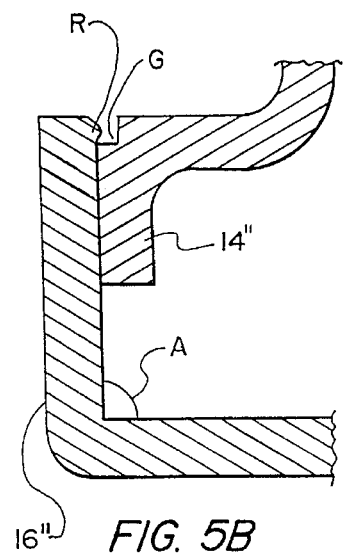
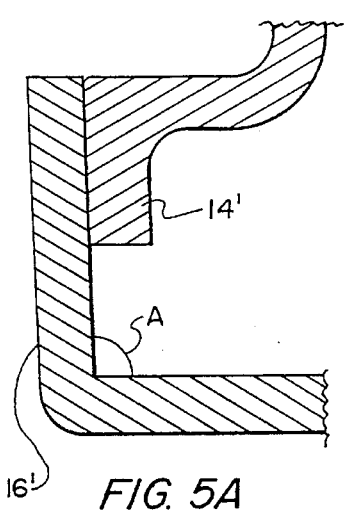
FIG. 2
FIG. 4
FIG. 5B
PRIOR ART
FIG. 1
FIG. 3
FIG. 5A

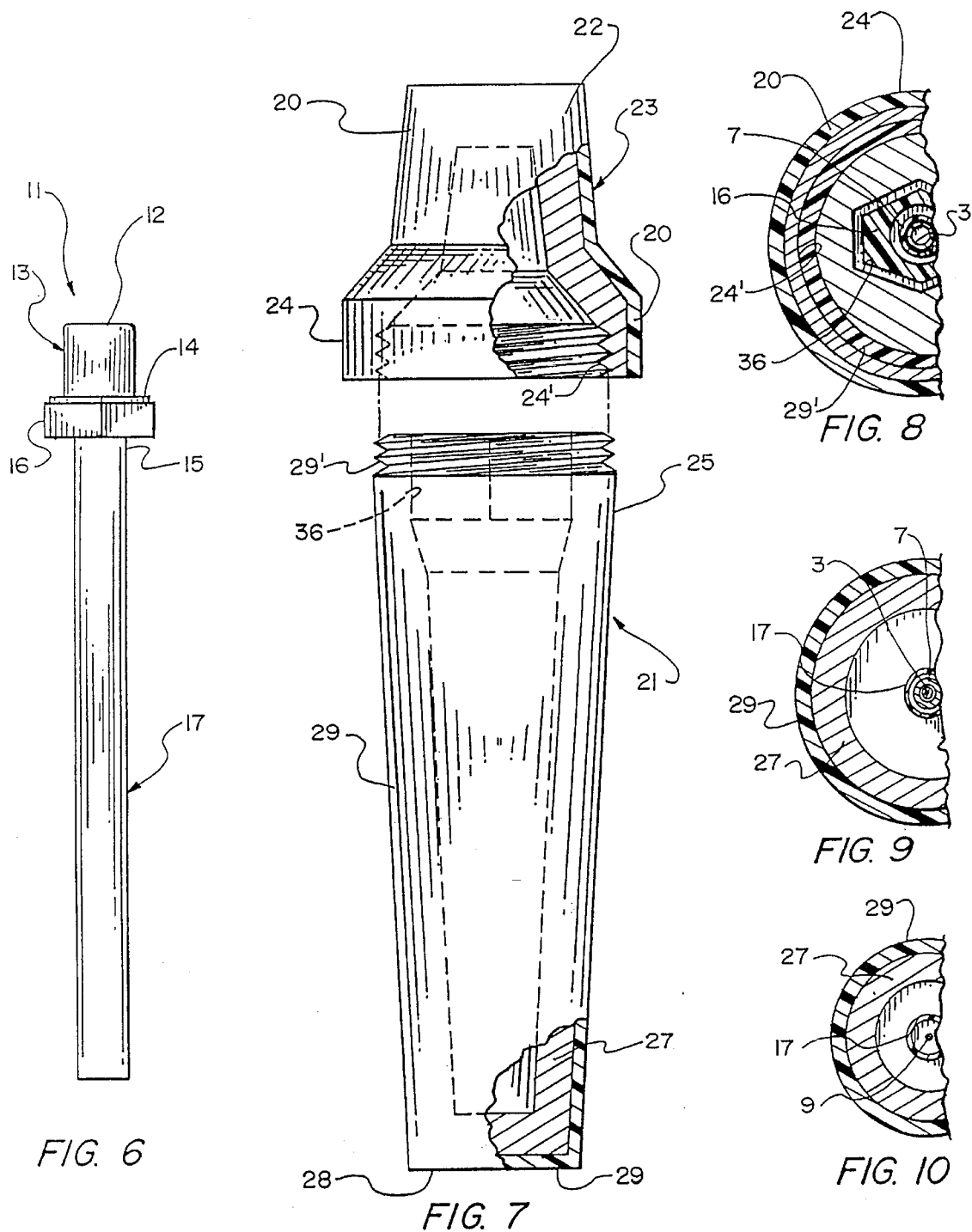

MEDICAL SYRINGE DISPOSAL

TECHNICAL FIELD

This invention relates to safe disposal of medical syringes and concerns especially containers conducive to such safe disposal, including such disposal of syringes containing radioactive residues.

BACKGROUND OF THE INVENTION

Many or most medical syringes nowadays are intended for single use only, and for disposal promptly thereafter, to guard against the possibility of contaminating a subsequent patient or a health care professional with the blood of any patient or with any residual medication in the syringe. Where a medication comprises radioactive material, special care must be taken to prevent not only leakage of blood or medication liquid from the syringe but also exposure of the surroundings to radiation.

Whereas collective disposal of used syringes with their needles and other "sharps" such as scalpels and stitch cutters is known, as in Haniff U.S. Pat. No. 4,657,139 and in McCarthy U.S. Pat. No. 5,273,221; the trend toward one-time usage is conducive to immediate individual disposal, for which packages are known, as in Clanton U.S. Pat. No. 4,979,616 and in Yates et al. U.S. Pat. No. 5,293,616. Such one-syringe packages are bulkier than containers known for new syringes, as in Windischman U.S. Pat. No. 4,106,622 and in Cuu U.S. Pat. No. 4,634,428; but packaging of new syringes does not include any provision for syringe disposal, so a new package is not convertible to a disposal package.

Yet a need exists for fluid leakproof disposal packages to hold individual used syringes, and a related need exists for radiation shielding in the packaging of such used syringes containing residues of radioactive medication. The present invention is directed toward meeting these and other related needs.

SUMMARY OF THE INVENTION

A primary object of the present invention is to provide a fluid leakproof package for used medical syringes individually.

Another object of this invention is to accommodate, lengthwise in such a package, a hypodermic needle mounted on one end of the syringe barrel.

A further object of the invention is to accommodate, lengthwise in such package, a plunger incompletely depressed into the barrel.

Yet another object of this invention is to provide a positive press-fit snap-lock leakproof structure for such a package.

A still further object of the invention is to shield the surroundings from radiation coming from radioactive residue in a used medical syringe, even when in a fluid leakproof package.

In general, the objects of the present invention are attained by providing a container adapted to enclose a used medical syringe and seal off its contents to protect the surroundings against fluid leakage therefrom. In a preferred embodiment, such a container has a two-piece tubular structure including press-fit leakproof junction of the open ends of the component pieces when forcibly juxtaposed.

More particularly, such fluid leakproof container is adapted to be used in combination with a radiation shielding container, to protect the surroundings from fluid and/or radiation contamination. For example, a press-fit fluid leakproof inner container is so used in combination with a twist-fit radiation shielding outer container.

Other objects of the present invention, together with means and methods for accomplishing the various objects, will be apparent from the following description and accompanying diagrams of a preferred embodiment being presented by way of example rather than limitation.

SUMMARY OF THE DRAWINGS

FIG. 1 is a side elevation of a conventional (prior art) disposable single-use medical syringe with attached needle, suitable for disposal according to this invention, as in subsequent views;

FIG. 2 is a plan view of the syringe of FIG. 1 (prior art);

FIG. 3 is an exploded side elevation of tubular components of a container of the present invention, open at adjacent ends but closed at opposite ends, adapted to be press-fit together and so assembled around the medical syringe and attached needle of preceding views;

FIG. 4 is a plan view of the container components of FIG. 3;

FIG. 5A is a transverse sectional detail (enlarged) of a first corner embodiment of an assembled container of this invention; and FIG. 5B is a transverse sectional detail (enlarged) of a second corner embodiment of an assembled container of this invention.

FIG. 6 is a side elevation of a container assembled from the container components of FIG. 3 by press-fitting their open ends into fluid leakproof relationship about a syringe (and needle) of FIG. 1;

FIG. 7 is an exploded side elevation of components of another container (partly cut-away) useful along with the container of the preceding views according to this invention, having open adjacent ends (opposite ends closed) adapted, as by threading, to be twisted together and so assembled around the the medical syringe container;

FIG. 8 is a transverse sectional elevation through a composite container at the junction of the FIG. 7 components assembled around the FIG. 6 container with the syringe of FIG. 1 inside;

FIG. 9 is a similar transverse sectional elevation through the mid-part of a lower portion of the same composite container; and FIG. 10 is a similar transverse sectional elevation through an even lower part of the same resulting composite container.

DESCRIPTION OF THE INVENTION

FIG. 1 shows, in side (or longitudinal) elevation, conventional (prior art) disposable single-use medical syringe 1, with attached needle 9, optionally surrounded by protective cover 10 (in phantom). The syringe itself has two main members: cylindrical barrel 7, and cylindrical plunger 3 fitting slidably into the barrel. The barrel is open at its plunger-receiving end 5, where it flares outward at opposite sides as finger-grip 6, and at its other end is constricted to tip 8 (open), where protective cover 10 encloses needle 9. The plunger is closed from its end 4 within the barrel and shown here nearly fully inserted, to its flared round (thumb-actuated) opposite exposed or top end 2. A person holding such syringe can fill it wholly or partially with medicating liquid by manually withdrawing the plunger (partially) from the barrel with the (uncovered) needle end immersed in the liquid, and contrariwise can dispense the liquid from the syringe (after de-aerating it) via the needle by squeezing thumb and fingers to depress the plunger further into the barrel.

FIG. 2 shows, in top plan, thumb-actuated end 2 of the syringe plunger, and finger-grip 6 (of the syringe barrel) protruding to the right, and left sides. Otherwise both the plunger and the barrel are hidden behind or below that top end so are not visible in this view.

FIG. 3 shows, in exploded side elevation, two-piece container embodiment 11 of this invention. Upper tubular container component 13 has cylindrical upper portion 12 closed hatlike overhead, and has adjacent tubular brim portion 14 of hexagonal outline open downward. Lower tubular container component 17 has, at upper end 15, similarly outlined portion 16 open cuplike upward and open axially downward to a long tubular body portion terminating in closed bottom end 18. Open lower end portion 14 of upper tubular component 13 is so dimensioned to enable it to be press-fit snugly within upper end portion 16 of lower tubular component 17, thereby providing the respective tubular container components with a fluid leakproof junction.

FIG. 4 shows, in plan the container components of FIG. 3, just as if assembled. A double hexagonal outline of upper end portion 16 of the lower component closely surrounds slightly smaller hexagonal lower end portion 14 of the upper component 13 with circular top 12.

FIGS. 5A and 5B show, in enlarged transverse section, a corner detail at a junction of two embodiments of the assembled components. A single prime in FIG. 5A, or a double prime in FIG. 5B, denotes a variant of a numbered part from preceding views. As shown, junction occurs upon insertion of the open end of the short upper component of the container within the open end of the longer lower component. Equivalent junctions might reverse the inner/outer end relationship. As suggested here, press-fit assembling of such ends together is facilitated, as by tapering the entering end slightly inward and/or tapering the receiving end slightly outward (e.g., several degrees), either method tending to increase included angle "A" of the latter.

In FIG. 5A, part of the inner wall surface of cupped upper end portion 16' of the lower component is snugly (leakproof) contiguous with the outer wall surface of the upper component's brim portion. FIG. 5B differs from FIG. 5A by detent or ridge R at the inner edge of the outermost rim of cupped upper end portion 16" of the lower component and by complementary indentation or groove G in the lower shoulder portion 14" of the upper component. An audible and tactile "snap" occurs when ridge R enters groove G, further assuring a leakproof junction of the container components, and deterring subsequent unintentional (or intentional) disassembly.

FIG. 6 shows in side elevation (reduced scale) fluid leakproof container 11 assembled from the FIG. 3 components by press-fitting the open end of upper component 13 into fluid leak-proof relation, within the open end of lower component 17. The assembled container is understood here to be enclosing a syringe (and needle) of FIG. 1. Further enhanced protection may be obtained, as by enclosing container 11 as an inner container within an outer container, to form a composite container effective to shield the surroundings from radiation contamination as well as to preclude leakage of residual fluid.

FIG. 7 shows, in longitudinally exploded side elevation (on a like scale) two-piece embodiment of radiation-shielding metallic container embodiment 21, whose upper component 23 has plastic outer skin layer 20. Outer hollow sombrero-shaped top portion 22 opens downward within enlarged brim portion 24, whose metallic internal perimeter 24' is threaded. Lower tubular container component 27 has plastic outer skin 29 including, at open upper end 25, portion 26 externally threaded complementarily to the open internally threaded overlying component. The metallic inner part of the lower component opens axially downward into long tubular body portion 27, tapering to closed bottom end 28. When so threaded together, components 23 and 27 fit snugly and provide a radiation-shielding container.

FIGS. 8, 9, and 10 show, in fragmentary transverse section at several levels, the composite container of this invention assembled from the outer (FIG. 7) container, enclosing the inner (FIG. 6) container, itself enclosing the FIG. 1 syringe (and residual contents).

FIG. 8 through the outer container junction shows (from outside in) upper component (23) skin layer 20, threaded inner wall 24', in mesh with threaded part 29' of lower component (21) skin layer 29. Recess 36 in body layer 27 of inner container (11) is hexagonal and accommodates similar horizontal portion 16 of the lower component of the inner container, shown sectioned just below the finger grip (not shown) of enclosed syringe barrel 7, and plunger 3 (both shown).

FIG. 9 shows a corresponding sequence of features through the mid-part of the same resulting composite container and its contents. Here the similarly directed sequence lacks the outer parts in FIG. 8 but shows skin 29 and body 27 of lower wall component 21 of the outer container, then the lower wall of inner container component 17, and finally cylindrical barrel 7 and plunger 3 of the syringe.

FIG. 10 resembles FIG. 9 at smaller diameter, and with needle 9 substituted for the syringe elements now above the plane of view.

Operation of the present invention will be apparent from the foregoing description and the accompanying diagrams as described and from the following additional remarks.

No unusual materials of construction are required. The syringe may be made of glass or organic polymeric material (plastic), or the plunger may be made of one such composition, and the barrel be made of another such composition. The needle is normally metallic. The inner container is preferably made of polymeric material, as suggested by the shading. The outer container's ability to shield the surroundings from radiation contamination is a function of mass, so its predominant composition is preferably lead, whose thickness is selected to meet acceptable radiation health and safety standards. Its outer skin may be metallic, such as steel, instead of plastic.

Instead of threaded turns as in the illustrated embodiment, an equivalent quicker-acting twist-fit junction (not shown) may have one component's transverse end surface vertically slotted and ramped to admit two or more evenly spaced balls on respective stems extending from the opposite component's like end surface, enabling the ends to be drawn together with a simple partial turn.

A principal benefit of the present invention is its assurance of relative freedom from contamination by potentially hazardous residual blood, drugs, and even radiation from radioactive residues on their way to final disposal. The inner container cannot be closed until the finger grip of the syringe is oriented to drop into the hexagonal open end, and once snap-locked shut it is precluded from re-opening. Other advantages are uniform and systematic handling of used medical syringes, and resulting savings, not least a reduction in costs of dealing with (or insuring against) possible economic consequences of personal encounters with harmful syringes and their residues through negligent handling or otherwise.

Preferred embodiments and variants have been suggested for this invention. Other modifications may be made, as by adding, combining, deleting, or subdividing compositions, parts, or steps, while retaining all or some of the advantages and benefits of the present invention-which itself is defined in the following claims.

I claim:

1. A syringe-disposal container, comprising a two-piece leakproof inner container including an upper tubular piece closed at its top end but open at its bottom end to accommodate a syringe piston and flared laterally outward at its open bottom end to accommodate a syringe barrel finger grip, and a lower tubular piece closed at its bottom end but open at its top end to accommodate a syringe barrel and flared laterally outward at its open top end to accommodate the finger grip, with respective flared open ends being adapted to be assembled together into press-fit sealing relationship about such finger grip; and a two-piece outer radiation-shielding container including an upper tubular piece closed at its top end and open at its bottom tubular end to accommodate the upper piece of the inner container, a lower tubular piece closed at its bottom end and open at its top end to accommodate the lower end of the inner container, the top surface of the lower tubular piece being recessed to accommodate the laterally flared press-fit ends of the inner container when the top and bottom pieces of the outer container are assembled together about the outwardly flared inner container.

2. A syringe-disposal container according to claim 1, wherein the two-piece inner container is adapted to be assembled by having its open ends press-fit together.

3. A syringe-disposal container according to claim 1, wherein at least one piece of the two-piece inner container includes a detent co-acting with an edge of the other piece, when assembled, to resist re-opening of the container.

4. A syringe-disposal container according to claim 1, with the outer container assembled about the assembled inner container by having its open ends assembled together.

5. A syringe-disposal container according to claim 1, with the outer container assembled in radiation-shielding relation about the assembled inner container.

6. A syringe-disposal container according to claim 5, with the inner container, in combination with a used syringe, sealed inside the inner container, shielded inside the assembled two-piece outer container.

* * * * *